United States Patent [19]
Castro

[11] Patent Number: 5,308,321
[45] Date of Patent: May 3, 1994

[54] RETAINER ASSISTED BY VACUUM EXPANSION SYSTEM

[76] Inventor: Donna J. Castro, 527 Ave. B, Redondo Beach, Calif. 90277

[21] Appl. No.: 878,832

[22] Filed: May 5, 1992

[51] Int. Cl.$^5$ ............................................. A61M 1/06
[52] U.S. Cl. ...................................................... 604/74
[58] Field of Search ..................... 604/73, 74, 75, 76; 128/869; 378/37

[56] References Cited

U.S. PATENT DOCUMENTS

| | | | |
|---|---|---|---|
| 1,847,658 | 3/1932 | Lasker | 604/74 |
| 2,542,505 | 2/1951 | Gascoigne | 604/74 |
| 4,705,504 | 11/1987 | Viers | 604/75 |
| 4,759,747 | 7/1988 | Aida | 604/74 |
| 4,772,262 | 9/1988 | Grant | 604/74 |
| 4,943,986 | 7/1990 | Barbarisi | 378/37 |
| 5,007,899 | 4/1991 | Larsson | 604/74 |
| 5,049,126 | 9/1991 | Larsson | 604/75 |

OTHER PUBLICATIONS

Large-core breast biopsy offers reliable diagnosis, by Steve H. Parker, M.D. and William E. Jobe, M.D., Diagnostic Imaging, Oct. 1990.
Stereotactic Breast Biopsy with a Biopsy Gun, by Steve H. Parker, M.D., et al., Radiology, Sep. 1990.
Nonpalpable Breast Lesions: Stereotactic Automated Large-Core Biopsies, by Steven H. Parker, et al., Radiology, Aug. 1991.
Fischer Imaging Corporation's promotional literature describing the "MAMMOTEST" equipment (publication date unknown).
Fischer Imaging Corporation's promotional literature describing the "ATHENA HF High Frequency Screening & Diagnostic Mammography System" (publication date unknown).

Primary Examiner—Michael A. Brown
Attorney, Agent, or Firm—Spensley Horn Jubas & Lubitz

[57] ABSTRACT

A cup-shaped member having a hollow interior in which at least a portion of a patient's breast is received. The retainer device further includes a suction port provided in communication with the interior of the cup member. The suction port is operable to be connected with a suction source for communicating suction pressure from the suction source into the interior of the cup member.

24 Claims, 2 Drawing Sheets

RETAINER ASSISTED BY VACUUM EXPANSION SYSTEM

BACKGROUND OF THE INVENTION

1. Field of the Invention

The present invention relates to apparatus and methods for retaining, stabilizing and expanding a portion of the body of a person or other biological organism and, in particular embodiments, a portion of a woman's breast, for medical examination, interventions, and/or hygienic shielding purposes.

2. Description of Related Art

Various systems for examining human breast tissue are known in the art. For example, x-ray mammography systems for taking x-ray images of breast tissue, have been used for quite some time to identify and locate tumors, growths or other anomalies in the breast or chest wall tissue. Typically, such systems employ two generally parallel plates arranged to squeeze the patient's breast therebetween to flatten and hold the patient's breast steady during the x-ray imaging process. This procedure can create severe discomfort for the patient. In addition, since the breast is covered by the two plates during the imaging process, interventional procedures (wherein a medical instrument is inserted into the breast tissue) are typically difficult and cumbersome during the imaging process or while the breast is held by the plates.

Other imaging processes employ flat, hard surfaces on which the patient's breast is pressed, to make the breast as flat as possible during the imaging process. Further processes employ specially designed tables having holes through which the patient's breasts are suspended. These various prior systems can be uncomfortable and sometimes painful to the patient. In addition, these systems may not provide enough support to hold the breast tissue steady during the imaging process. Since the breast tissue is relatively flexible and difficult to stabilize, an anomaly detected by an imaging system may be difficult to locate with an intervention instrument (such as a needle).

In addition to x-ray imaging systems, other imaging systems are known in the art, including ultrasound systems and magnetic resonance imaging (MRI) systems. However, many of these known systems do not employ any suitable mechanism for holding the breast tissue stable during the imaging process, and therefore, may render it difficult to locate an anomaly detected by the imaging process with an intervention instrument. While it is known in some MRI systems to employ a bra-type device for holding the breast, such devices do not stabilize the tissues when an intervention instrument is used on the breast.

Thus, some of the known systems discussed above employ mechanisms for holding a patient's breast steady during an imaging process, but can be extremely uncomfortable to the patient. Furthermore, some of these systems cannot be used with an intervention instrument (for insertion into the breast tissue) while the breast is held in position during an imaging process. Thus, in various known systems, it may be difficult to find with an intervention instrument the same location in the breast tissue at which an anomaly is detected from an image produced by the imaging system. Furthermore, in various known systems, such as those discussed above, it is a common practice to directly contact the skin of the breast with, for instance, table surfaces, panel surfaces or other portions of the imaging apparatus. This raises hygienic concerns and may require extensive sterilization of portions of the imaging instruments prior to each use thereof.

SUMMARY OF THE INVENTION

The present invention relates to a retainer device and method which, in certain embodiments, is designed to retain, expand and stabilize a patient's breast or other anatomical part, for medical examination purposes. According to the illustrated embodiments, a retainer device employs a cup-shaped member having a hollow interior in which at least a portion of a patient's breast is received. The retainer device further includes a suction port provided in communication with the interior of the cup member. The suction port is operable to be connected with a suction source for communicating suction pressure from the suction source into the interior of the cup member.

Due to suction pressure communicated to the interior of the cup member, the breast portion received in the cup member is expanded such that the skin of the breast becomes fixed against the inner peripheral wall of the cup member. In this manner, the breast is held stationary for an imaging or interventional procedure. When used in conjunction with an x-ray apparatus, the material from which the cup member is made is translucent to x-rays. When used in conjunction with an MRI apparatus, the cup member is made of a material which has a low magnetic susceptibility. The cup member may be made of a material which is suitable for use with an ultrasonic imaging apparatus.

Further embodiments include apertures provided in the cup member through which instruments may pass for contact with or insertion into the breast tissue. Indicia markings may be provided on or in the cup member to divide the cup member into discrete sections. The indicia markings may be used to enhance the ability to determine the location of an anomaly detected on an image formed by the imaging apparatus. In preferred embodiments, the indicia is visible on the image formed by the imaging apparatus.

BRIEF DESCRIPTION OF THE DRAWINGS

The detailed description of embodiments of the invention will be made with reference to the accompanying drawings, wherein like numerals designate corresponding parts in the several figures.

DETAILED DESCRIPTION OF THE PREFERRED EMBODIMENTS

The following detained description is of the best presently contemplated mode of carrying out the invention. This description is not to be taken in a limiting sense, but is made merely for the purpose of illustrating general principles of embodiments of the invention. The scope of the invention is best defined by the appended claims.

As noted above, the present invention relates to a retainer system for retaining, stabilizing and expanding a portion of a patient's body. The patient may be a human or other biological organism. Various embodiments discussed below are designed for retaining a portion of a woman's breast. However, it will be recognized that principles of the present invention are applicable for systems for retaining portions of other parts of the body of a woman, man or child or other animal. In this regard, the cup member of the system discussed below may be formed in a configuration suitable for receiving the breast of other types of animals or for receiving other anatomical parts of the body of a human or other animal. However, since embodiments of the present invention have significant utility in the field concerned with medical examinations and interventions of a woman's breast, the following discussion of illustrated embodiments is directed to breast retention systems for retaining a woman's breast.

Figure 1:
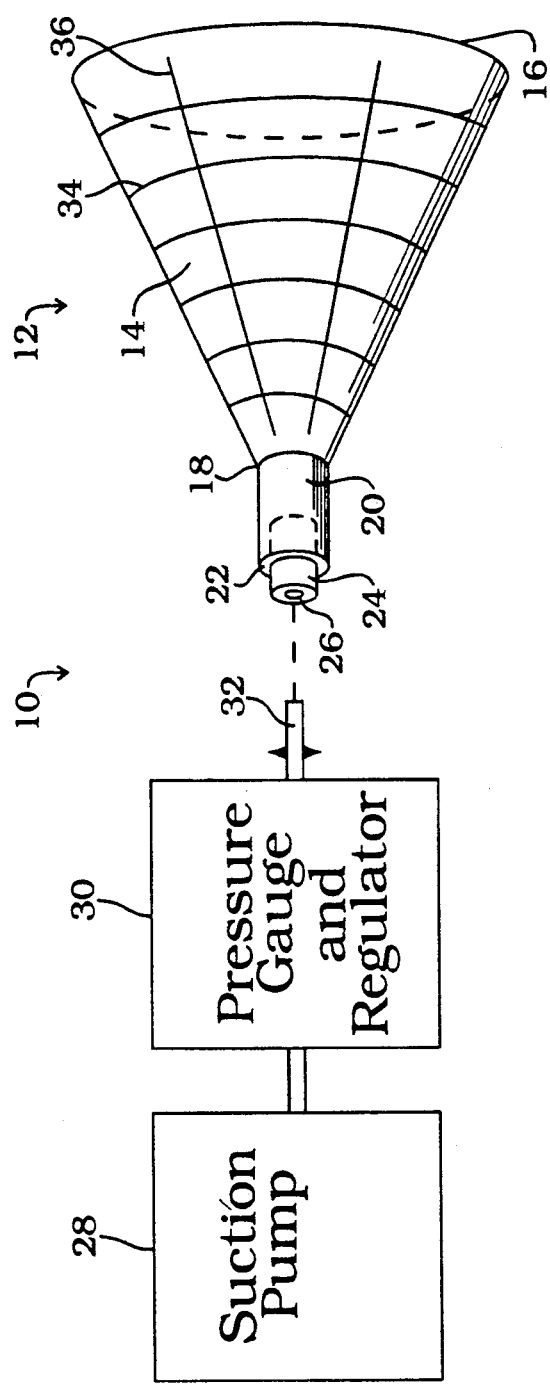
FIG. 1 is a perspective view of a retainer and a block diagram of a suction system according to a first embodiment of the invention.

FIG. 1 shows a first embodiment of a breast retaining system for retaining a breast for medical examination purposes. The system, generally indicated at 10, includes a breast retainer, generally indicated at 12. Retainer 12 is composed of a cup member 14 having a hollow interior for receiving at least a portion of a woman's breast (not shown). The cup member 14 includes a large diameter end 16 having a relatively large diameter opening through which the breast may be inserted. Cup member 14 has a small diameter end 18. The cup member 14 is tapered between the small diameter end 18 and the large diameter end 16. Extending from the small diameter end 18 is a hollow, generally cylindrical port structure 20. The hollow interior of the port 20 opens at one end into the hollow interior of the cup member 14. The opposite end 22 of the port 20 is open and has, received therein, a port reducing member 24.

The port reducing member 24 comprises a generally cylindrical dowel having an outer diameter equal to the inner diameter of end 22, so as to be snugly fit within end 22 as shown in FIG. 1. The generally cylindrical portion of the port 20 may be tapered between end 22 and cup member end 18, so as to be slightly larger in diameter at the cup member end 18 than at end 22. The port reducing member 24 includes a suction port aperture 26 extending through the entire length of the member 24, so as to provide a flow communication path into the interior of the cup member 14.

The system 10 further includes a suction pump 28, a pressure gauge and regulator 30 and a suction hose 32. The suction hose 32 is connectable to the suction port aperture 26, e.g., by inserting a portion of suction hose 32 into the suction port aperture 26. The suction hose 32 is connected, through the pressure gauge and regulator 30 to the suction pump 28. In this manner, the suction pump 28 provides a suction pressure which is communicated through the suction hose 32 into the interior of the cup member 14. The pressure gauge and regulator 30 regulates the suction pressure and provides a readable display for indicating the suction pressure communicated through suction hose 32.

In operation, the cup member 14 is placed over at least a portion of the patient's breast (or the entire breast), such that the breast portion is received within the interior of the cup member 14. Suction pressure is then applied via suction pump 28, through suction tube 32 into the interior of the cup member 14. The suction pressure is regulated so as to provide a suitable vacuum pressure for expanding the breast such that the skin of the breast is pressed against and fixed to the inner peripheral wall of the cup member 14. In this manner, the breast portion is held steady and snugly within the cup member 14. Preferably, the suction pressure is regulated so as to provide minimal or no discomfort to the patient. While being held stationary with respect to the cup member 14, the breast portion may be examined, e.g., by various known types of imaging apparatus such as x-ray imaging, ultrasonic imaging, MRI and/or positron emission tomography (PET) scanner systems.

In preferred embodiments, the cup member 14 is provided with indicia markings, for example, a plurality of circumferencial indicia markings 34 arranged around the circumference of the cup member 14 and a plurality of radial indicia markings 36 arranged approximately perpendicular to the circumferencial indicia markings 34. These markings divide the breast portion received within the cup member 14 into discrete sections for easier identification of locations on or in the breast. It will be understood that other patterns of indicia markings may be used as an alternative to the circumferencial and radial indicia markings shown in FIG. 1.

When used with an x-ray imaging apparatus, cup member 14 is preferably made of the material which is generally translucent to x-rays. In preferred embodiments, indicia markings, such as markings 34 and 36, are not fully translucent to x-rays such that these markings would be clearly visible on an image formed by the x-ray apparatus. In this manner, an x-ray apparatus may be positioned so as to provide an x-ray image of the breast portion received within the cup member 14, while the indicia markings 34 and 36 will be visible on the x-ray image, so as to divide the image of the breast portion into discrete sections for more easily identifying the location of an anomaly in or on the breast portion.

Similarly, the system 10 may be used with an ultrasonic imaging apparatus, wherein the cup member 14 is made of material which will be substantially invisible in an image formed by the ultrasonic apparatus. In preferred embodiments of such a system, the indicia markings 34 and 36 will be made with a material which is visible on an image formed by the ultrasonic apparatus.

When the system 10 is to be used with an MRI apparatus, the cup member 14 is preferably made of a material which has a relatively low magnetic susceptibility so as to be substantially invisible in the image formed by the MRI apparatus. In preferred embodiments, the indicia 34 and 36 may be made of a material which has a higher magnetic susceptibility so as to be visible in the image formed by the MRI apparatus.

Figure 2:
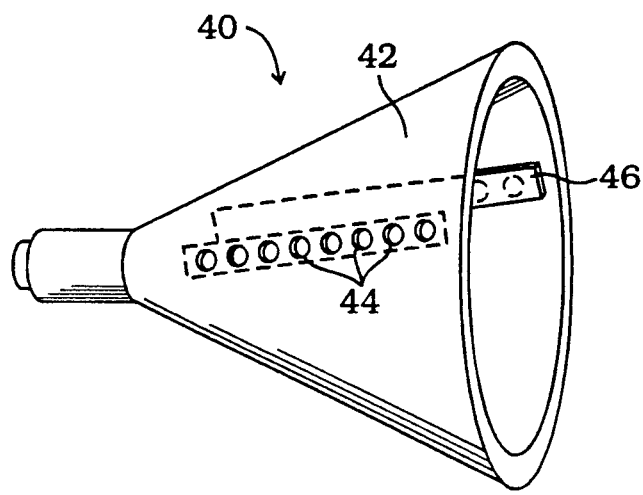
FIG. 2 is a perspective view of a retainer according to a second embodiment of the invention.

FIG. 2 shows a further embodiment of a retainer for use in a system such as discussed above with respect to system 10. In FIG. 2, the retainer is generally indicated at 40 and includes a cup member 42 similar to cup member 14 discussed above. Cup member 42 may or may not be provided with indicia as discussed above with respect to cup member 14. However, unlike cup member 14 discussed above, cup member 42 is provided with a plurality of access holes 44 therethrough. In FIG. 2, the access holes 44 are arranged in two linear arrays, each array extending between the large and small diameter ends of the cup member 42. These access holes 44 are provided for allowing a medical instrument, such as a surgical instrument or needle, to pass through the cup member 42 and either contact or penetrate the breast portion received within the cup member 42.

Thus, following or during an imaging procedure, a medical instrument can be inserted through the access holes 14. In this manner, the image formed by an imaging apparatus (such as an x-ray apparatus, an ultrasonic apparatus, or an MRI apparatus) can be used to identify an anomaly on or in the breast portion. The location of the anomaly can be readily determined, by virtue of the indicia markings 34 and 36. A medical instrument can be inserted into the breast portion to the location of the anomaly, so as to take a sample or biopsy of the tissue at the location of the anomaly and possibly destroy it by delivered energy while the breast is held stationary (and fixed with respect to the indicia markings 34 and 36) within the cup member 42.

In preferred embodiments, a layer of sealing material 46 may be arranged over the access holes 44, either inside or outside of the cup member 42. In the FIG. 2 embodiment, two layers 46 are provided along the inner peripheral wall of the cup member 42 over the access holes 44. Sealing layers 46 may be made of, for example, rubber or any other suitable sealing material which allows a medical instrument to pass therethrough while still retaining a suitable seal for the suction pressure applied to the cup member interior. While the FIG. 2 embodiment employs two linear arrays of access holes 44 and two strips of sealing material layers 46, it will be understood that other arrangements of access holes and corresponding sealing material may be employed in further embodiments.

Figure 3:
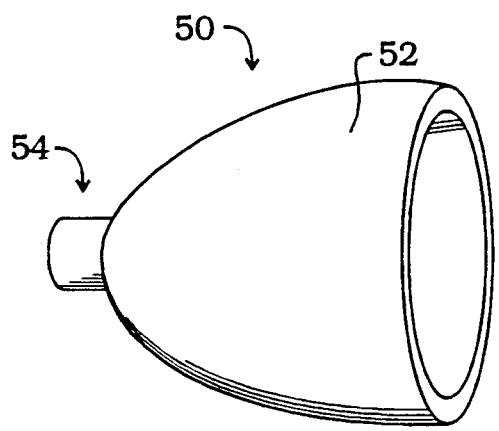
FIG. 3 is a perspective view of a retainer according to a third embodiment of the invention.

The cup members 14 and 42 in the FIG. 1 and FIG. 2 embodiments may be made of a rigid or semi-rigid material, such as a suitable plastic material, however, it is also contemplated that flexible materials may be used in certain embodiments. FIG. 3 shows an embodiment of a retainer 50 which employs a cup member 52 made of a generally flexible material, such as natural or synthetic rubber. Cup 52 is shaped to closely conform to the shape of a breast portion received herein. It will be recognized that the embodiments shown in FIGS. 1 and 2 may be also be configured to more closely conformed to the shape of the breast portion received therein. With respect to FIG. 3, the cup member 52 is designed to provide a close fitting, prophylactic-style covering for the breast portion, e.g., received therein so as to provide a generally hygienic shield for the breast portion during various examination procedures. The cup member 52 may or may not be provided with indicia as discussed above with respect to cup member 14. In further embodiments, the prophylactic-style cup member 52 may have a sealed end instead of the suction port end 54 shown in FIG. 3. In such an arrangement, the prophylactic-style of cup member 52 can serve as a hygienic covering to protect the breast portion received therein during various examination procedures, such as during the known imaging procedures discussed above in the Related Art section.

It will be understood that various cup member shapes may be used with embodiments of the invention discussed above. For example, a simple, clear, semi-rigid cup member with a shape which will keep the breast portion uniformly flat may be employed for standard mammography systems. In systems which employ suction pressure, a lubricant (e.g., with an antiseptic and/or anesthetic drug) may be applied to the inner peripheral wall of the cup member or to the breast portion, prior to receiving a breast portion within the cup member so as to improve the pressure seal between the cup member and the breast portion. When antiseptic and anesthetic drug is contained in the lubricant, the lubricant can reduce the chances of an infection and improve anesthesia during insertion of a needle. Furthermore, in systems which employ suction pressure, a fluid collection system may be used in conjunction with the suction port aperture 26 so as to collect fluid discharge from the nipple and/or other anatomical areas of the patient, e.g., for histopathological studies and/or cultures. In this regard, a further suction tube (not shown) may be added to the suction tube 32, e.g., adjacent thereto or coaxially therewith for the collection of fluid samples with an improved ability to withstand bacterial contamination.

In systems which employ suction pressure, a temperature regulator device 38 may be used in conjunction with the suction port aperture 26 or the cup member wall so as to lower the temperature of the portion of the patient's anatomy received by the cup member. This will operate to enhance the rigidity of the tissue when a medical instrument is inserted.

While the embodiments above are discussed with relation to examination and protection of a patient's breast, it will be understood that further embodiments may be designed to hold and expand other areas of overlying skin in a fixed and predetermined shape for imaging and/or for contact and insertion of a medical instrument. Thus, embodiments may be used for imaging or other examination procedures, where an anatomical area such as the skull or other area needs to be held in a fixed position for invasive and/or open procedures. The above discussed systems may be used for detection and examination of a patient's breast, chest wall, or other areas for tumors, growths, calcifications, dilatations of vessels or ducts, tissue anomalies, abnormalities in vessels, ducts or lymph glands or nodes, or other anomalies. Embodiments of retainers as discussed above may be simple and economical to manufacture and may be made so as to be disposable in further preferred embodiments. Embodiments of the system are designed to comfortably and positively retain a portion of the anatomy of a patient in a fixed position relative to the retainer and to indicia markings on the retainer and/or may provide hygienic shielding for the anatomical portions during a medical procedure.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore considered in all respects as illustrative and not restrictive, the scope of the invention being illustrated by the attended claims rather than the foregoing description and all changes which come within the meaning and range of equivalency of the claims are therefore intended to be embraced therein.

What is claimed is:

1. A retainer operable with a suction source for retaining a portion of a patient's anatomy for at least one of an examination and engagement with a medical instrument, the retainer comprising:
   a cup member having an interior configured to receive at least a portion of a patient's anatomy therein; and
   a suction port provided in communication with the interior of the cup member and operable to be connected to the suction source for communicating suction pressure from the suction source into the interior of the cup member to expand the portion of a patient's anatomy received therein;

wherein the cup member has at least one wall defining the cup member interior and a plurality of indicia lines provided on the wall with each of said indicia lines crossing at least one other of said indicia lines to define a plurality of discrete wall areas bordered by said indicia lines.

2. A retainer as recited in claim 1, wherein the indicia comprises a plurality of circumferencial lines extending parallel with each other about the circumference of the wall and a plurality of radial lines traversing the circumferential lines.

3. A retainer as recited in claim 2, wherein the indicia comprises a plurality of lines defining a plurality of individual generally rectangular areas on the wall.

4. A retainer as recited in claim 1, wherein the wall of the cup member is made of a material which is substantially translucent to x-rays.

5. A retainer as recited in claim 1, wherein the wall of the cup member is made of a material which is substantially translucent to x-rays, and wherein the indicia is visible on x-ray images.

6. A retainer as recited in claim 1, wherein the wall of the cup member is made of a material which is substantially translucent to magnetic resonance images.

7. A retainer as recited in claim 1, wherein the wall of the cup member is made of a material which is substantially translucent to magnetic resonance images and wherein the indicia is visible on magnetic resonance images.

8. A retainer as recited in claim 1, wherein the at least one cup member wall is provided with at least one aperture for allowing an instrument to pass to the interior of the cup member upon a portion of a patient's anatomy being received in the interior of the cup member.

9. A retainer as recited in claim 8, further comprising a pressure seal for sealing the at least one aperture to inhibit loss of suction pressure through the at least one aperture.

10. A retainer as recited in claim 9, wherein the at least one wall of the cup member has an interior surface facing the interior of the cup member and the pressure seal comprises a rubber member disposed over the at least one aperture on the interior surface of the wall.

11. A retainer as recited in claim 1, wherein the at least one wall of the cup member has a plurality of apertures through which an instrument may pass to the cup member interior.

12. A retainer as recited in claims 1, wherein the suction port comprises a generally cylindrical tip extending from the cup member and defining an opening extending into the cup member interior.

13. A retainer as recited in claims 12, wherein the suction port further comprises a generally cylindrical port reducing member fitted within the opening of the generally cylindrical shaped tip of the suction port and having a passage provided in communication with the cup member interior.

14. A retaining system for retaining a portion of a patient's anatomy for at least one of an examination and engagement with a medical instrument, the retaining system comprising:

a suction source for providing suction pressure;

a cup member having at least one cup wall defining a cup interior configured to receive the portion of the patient's anatomy, the cup wall having at least one aperture for allowing an instrument to pass to the interior of the cup member upon a portion of the patient's anatomy being received in the interior of the cup member;

a suction port provided in communication with the interior of the cup member;

conduit connecting the suction source with the suction port for communicating suction pressure provided by the suction source to the interior of the cup member; and a pressure regulator for regulating the suction pressure communicated to the interior of the cup member to a pressure suitable for expanding the portion of the patient's anatomy received in the interior of the cup member.

15. A retainer as recited in claims 14, wherein the portion of the patient's anatomy comprises a portion of the patient's breast, the system further comprising a vacutainer tube provided in communication with the cup member interior for collecting fluid discharge from the nipple of the breast received in the cup member interior.

16. A retainer as recited in claims 15, wherein the vacutainer tube is provided along the conduit.

17. A retainer as recited in claims 14, wherein a temperature regulator is placed along the conduit to cool the air flow delivered to the portion of the patient's anatomy to enhance rigidity of the tissues.

18. A method for retaining a portion of a patient's anatomy for at least one of examination and engagement with a medical instrument, the method comprising the steps of:

providing a cup member having an interior;

receiving a portion of a patient's anatomy in the interior of the cup member;

applying suction pressure to the interior of the cup member to expand and stabilize the portion of the patient's anatomy received in the cup member; and forming an image of the portion of the patient's anatomy while the portion of the patient's anatomy is received within the cup member interior with at least one of an x-ray device, an MRI device, a PET scanner and an ultrasound device.

19. A method as recited in claim 18, wherein the step of applying suction pressure comprises the step of regulating the suction pressure to expand the portion of the patient's anatomy received in the cup member by an amount sufficient to fix the skin of the anatomy portion to the interior surface of the cup member.

20. A method as recited in claim 18, further comprising the step of passing an instrument through an aperture in the cup member to contact the portion of the patient's anatomy received in the cup member.

21. A method as recited in claim 18, further comprising the step of providing indicia on the cup member for sectioning the surface of the cup member into plural predefined areas.

22. A retainer for retaining a portion of a patient's anatomy for at least one of an examination and engagement with a medical instrument, the retainer comprising:

a cup member having an interior configured to receive at least a portion of a patient's anatomy therein; and a suction source provided in communication with the interior of the cup member to communicate suction pressure into the interior of the cup member to expand that portion of a patient's anatomy received therein;

wherein the cup member has at least one wall defining the cup member interior, the at least one wall having at least one aperture for allowing an instrument to pass to the interior of the cup member upon a portion of a patient's anatomy being received in the interior of the cup member.

23. A method for retained a portion of a patient's anatomy for at least one of examination and engagement with a medical instrument, the method comprising the steps of:

provided a cup member having a cup wall defining a cup interior, the cup wall having at least one aperture through which an instrument may pass to the cup interior;

receiving a portion of a patient's anatomy in the cup interior;

applying suction pressure to the interior of the cup member to expand and stabilize the portion of the patient's anatomy received in the cup member; and passing an instrument through the at least one aperture to contact the portion of the patient's anatomy received in the cup member.

24. A method for retained a portion of a patient's anatomy for at least one of examination and engagement with a medical instrument, the method comprising the steps of:

providing a cup member having a cup wall defining a cup interior, the cup wall having a plurality of indicia lines, with each of said indicia lines crossing at least one other of said indicia lines to define a plurality of discrete wall areas bordered by said indicia lines;

receiving a portion of a patient's anatomy in the cup interior;

applying suction pressure to the interior of the cup member to expand and stabilize the portion of the patient's anatomy received in the cup member; and associating various areas of the portion of the patient's anatomy received in the cup member with various discrete wall areas defined by the indicia lines.

* * * * *